United States Patent
Affre et al.

(10) Patent No.: US 11,051,687 B2
(45) Date of Patent: Jul. 6, 2021

(54) MACHINE FOR TREATING A MEDICAL APPARATUS

(71) Applicant: Ecolab USA Inc., St. Paul, MN (US)

(72) Inventors: Christian Affre, Allauch (FR); Jean-François Biry, Aix en Provence (FR); Sébastien Ruiz, Rognac (FR)

(73) Assignee: Ecolab USA Inc., Saint Paul, MN (US)

( * ) Notice: Subject to any disclaimer, the term of this patent is extended or adjusted under 35 U.S.C. 154(b) by 203 days.

(21) Appl. No.: 16/465,945

(22) PCT Filed: Dec. 11, 2017

(86) PCT No.: PCT/FR2017/053488
§ 371 (c)(1),
(2) Date: May 31, 2019

(87) PCT Pub. No.: WO2018/104690
PCT Pub. Date: Jun. 14, 2018

(65) Prior Publication Data
US 2020/0077877 A1    Mar. 12, 2020

(30) Foreign Application Priority Data
Dec. 9, 2016 (FR) ...................... 16 62203

(51) Int. Cl.
*A61B 1/12* (2006.01)
*A61L 2/18* (2006.01)
(Continued)

(52) U.S. Cl.
CPC ............... *A61B 1/123* (2013.01); *A61L 2/18* (2013.01); *A61L 2/24* (2013.01); *B08B 3/08* (2013.01);
(Continued)

(58) Field of Classification Search
None
See application file for complete search history.

(56) References Cited

U.S. PATENT DOCUMENTS 5,958,336 A      9/1999  Duarte
2015/0164602 A1  6/2015  Vasquez et al.
(Continued)

FOREIGN PATENT DOCUMENTS

CN    201684667 U    12/2010
CN    202055706 U    11/2011
(Continued)

OTHER PUBLICATIONS

International Patent Application No. PCT/FR2017/053488, International Search Report and Written Opinion dated Mar. 21, 2018, 13 pages (including 3 pages English translation of the International Search Report).

*Primary Examiner* — Cristi J Tate-Sims
(74) *Attorney, Agent, or Firm* — Fredrikson & Byron, P.A.

(57) ABSTRACT

A machine for treating a medical apparatus, such as an endoscope washer-disinfector, can be integrated into a wall at an opening of the wall. The wall can separate a first enclosure with a controlled/non-controlled atmosphere from a second enclosure with a non-controlled/controlled atmosphere. The machine may include first and second openings configured to allow the medical apparatus to be loaded into/unloaded from the machine. The machine may also include first and second doors sealingly closing the openings. The machine may include a partitioning interface attached to the wall that closes the opening in the wall and a movable part that can be removed from the partitioning interface. The movable part can at least partially carry a pump and solenoid valve of the treatment system. The movable part can be positioned immediately adjacent to the partitioning interface when the treatment machine is in an operating position.

13 Claims, 4 Drawing Sheets

(51) Int. Cl.
*A61L 2/24* (2006.01)
*B08B 3/08* (2006.01)
*A61B 90/70* (2016.01)

(52) U.S. Cl.
CPC ... *A61B 2090/701* (2016.02); *A61L 2202/121* (2013.01); *A61L 2202/122* (2013.01); *A61L 2202/14* (2013.01); *A61L 2202/15* (2013.01); *A61L 2202/17* (2013.01); *A61L 2202/24* (2013.01); *B08B 2203/0223* (2013.01)

(56) References Cited

U.S. PATENT DOCUMENTS

2015/0290349 A1* 10/2015 Lanzoni ............... A61B 1/123
    422/301
2016/0302654 A1* 10/2016 Ogawa ................. A61B 1/123

FOREIGN PATENT DOCUMENTS

| | | |
|---|---|---|
| CN | 102383701 A | 3/2012 |
| CN | 102974585 A | 3/2013 |
| CN | 203107764 U | 8/2013 |
| CN | 104204334 A | 12/2014 |
| CN | 104420790 A | 3/2015 |
| CN | 204699085 U | 10/2015 |
| CN | 205078776 U | 3/2016 |
| EP | 1588719 A1 | 10/2005 |
| EP | 2925373 B1 | 10/2015 |
| EP | 3620180 A1 * | 3/2020 ............. A61B 1/123 |
| JP | 2002065820 A | 3/2002 |
| RU | 2073526 C1 | 2/1997 |
| RU | 2353396 C2 | 4/2009 |
| WO | 2014083524 A1 | 6/2014 |
| WO | 2016087244 A1 | 6/2016 |
| WO | 2016141874 A1 | 9/2016 |
| WO | 2016186502 A2 | 11/2016 |

* cited by examiner

MACHINE FOR TREATING A MEDICAL APPARATUS

This application is a 35 U.S.C. 371 national phase filing from International Application No. PCT/FR2017/053488, filed Dec. 11, 2017, which claims the benefit of French Patent Application No. 16 62203, filed on Dec. 9, 2016. The entire contents of these applications are incorporated herein by reference.

The invention relates to a machine for treating a medical apparatus, as well as a set including a treating machine and a wall separating a first enclosure with a controlled/non-controlled atmosphere from a second enclosure with a non-controlled/controlled atmosphere. The invention also includes a maintenance procedure for a machine for treating a set according to the invention.

The invention falls under the domain of machines for treating medical apparatuses, and more specifically endoscope washer-disinfector (EWD).

Here the invention focuses on the EWD that a person skilled in the art usually refers to as a "pass-through" EWD type, in that this machine is integrated via a separation wall. These machines are meant to be integrated to the opening of a wall separating a controlled-atmosphere enclosure (for example the enclosure of an operating room for which the controlled atmosphere is typically purified by filtration and extraction) from an enclosure with non-controlled atmosphere, like a service room, and may contain contaminants (bacteria) suspended in the air.

This type of EWD most notably presents a loading door, on the side of the enclosure with the non-controlled atmosphere, allowing for example the loading of the contaminated endoscopes from this side, directly in the EWD treatment tank from a first opening of the tank, and another door, on the controlled atmosphere side, which makes it possible to collect the disinfected endoscope from this side (i.e. the operating room), from a second opening in the tank diametrically opposite of the first opening. It is also possible to load the contaminated endoscope from the controlled atmosphere enclosure and unload it on the non-controlled atmosphere enclosure side.

This machine is presented in the form of a contiguous furnishing, including particularly:
  A frame
  The loading tank, including its two access doors
  The treatment system, presenting the treatment circuit(s) including the pump(s), the conduit(s) and the solenoid valves, and any buses, making it possible to treat the interior and exterior surfaces of the endoscopes contained in the processing tank from a reservoir of disinfecting solution,
  The programmable controller controlling the treatment system, particularly the system's motor and solenoid valves, and for implementing a disinfecting cycle.

Most notably, the "pass-through" type EWD frame is integrated to the through-opening of the separation wall, by creating a seal between the two atmospheres, respectively the controlled and non-controlled ones.

Certain heavy maintenances of the EWD can be done on site, but on the contrary they entail completely removing the frame in order to review/repair it in the workshop. In this case, removing the frame completely frees the opening of the separation wall, thus losing the seal and the guarantee of the control of the air quality in the controlled-atmosphere enclosure, such as an operating room. Thus, and according to the invention's findings, for the design of the pass-through EWD known in the state of the art, the operating room is unusable after the EWD is removed and until the frame is replaced back in the separation opening.

This kind of pass-through EWD is, for example, known from the document WO 2014/083524 A1.

The purpose of this invention is to offer an endoscope treatment machine, such as an EWD with a treatment tank that has two opposite openings making it possible to load/unload from both sides of a wall meant to separate an enclosure with a controlled atmosphere from an enclosure with a non-controlled atmosphere, while allowing the control of the air quality of the controlled atmosphere, even in the case of heavy maintenance requiring this equipment to be removed.

Another purpose of this invention is to propose, at least through a embodiment, a machine that meets this objective, with increased security, limiting the manipulation needed to reach this objective.

Other objectives and advantages will be described below only as examples, and do not aim to limit the invention.

First of all, the invention concerns a machine for treating medical apparatuses, such as an endoscope washer-disinfector, to be integrated on a wall. The said separation wall is at a through-opening on the separation wall, separating a first enclosure with a controlled/non-controlled atmosphere from a second enclosure with a non-controlled/controlled atmosphere, the said machine including:
  A treatment tank including a first opening configured to allow the loading/unloading of a medical apparatus from the first enclosure and a second opening configured to allow the loading/unloading of a medical apparatus from the second enclosure,
  A first door system making it possible to sealingly close the first opening,
  A second door system making it possible to sealingly close the second opening,
  A treatment system of a medical device presenting one or several treatment circuits, including one or more pumps, one or more solenoid valves, allowing the interior and exterior surfaces of the medical device to be treated in the treatment tank by immersion or spraying from a disinfectant solution taken from a reservoir outside of the treatment tank.
  A programmable controller controlling the treatment system, particularly the motor and solenoid valves of the system, configured to implement the disinfection cycle of a medical apparatus.

According to the invention, the said machine includes:
  A partitioning interface to be integrated onto the wall and configured so to seal the opening of the wall, the said partitioning interface including at least one through-opening intended to face the second opening of the tank, at least in the operating position of the treatment machine, the second door system being secured to the said partitioning interface, locking in its closing position the said opening of the partitioning interface,
  A movable part, removable from the partitioning interface including a self-supporting chassis holding at least a part of the pump(s) and solenoid valves of the said system for treating the medical apparatus as well as the said programmable controller system, which, when the treatment machine is in operating position, is configured to position itself immediately adjacent to the enclosure interface, in such a way that allows during maintenance on the treatment system the removal of the movable part of the treatment machine while the said partitioning interface of the treatment machine still locks the wall opening, the partitioning interface opening thus being locked by the second door system. According to these optional characteristics of the invention, taken alone or combined:

The movable part onboards the treatment tank, a joint system secured to the movable part and/or secured to the partitioning interface, providing air tightness between the second opening of the tank and the corresponding opening of the partitioning interface in the treatment machine's operating position for which the second opening is superimposed on the partitioning interface, through the intermediary of the said joint system and allowing the removal of the movable part when removed or, alternatively;

The treatment tank is secured to the partitioning interface, a hydraulic connection making it possible to connect the tubes or the treatment system circuit(s) boarded onto the movable part, with the tubes or circuits of the treatment tank in the said position for using the treatment machine, and disconnecting them when removing them from the movable part;

The partitioning interface includes an enclosure intended to extend along the opening of the wall by locking it, as well as a peripheral fixation system secured to the enclosure, intended to run along the strip of the wall opening, along its mounts and even its upper edge;

The peripheral fixation system includes, for each opening mount, a first element, the support intended to press one side of the wall, and a second element, the counter-support meant to press the other side of the wall, as well as a control and/or tightening (e.g. by screw) system, configured to adjust the space between the first element and the second element from the thickness of the wall, or even make it possible to tighten the wall between the first element and the second element;

The partitioning interface includes a peripheral framework, serving as a cache, intended to run from the side of the enclosure's interface against which the chassis of the movable part is supposed to be, in position for using the length of the strip of the wall opening by covering them, then protruding beyond the face of the movable part of the wall side, the inner walls of the frame forming a space for the removable part, with a width adjusted to the size of the movable part;

The self-support chassis of the movable part is a frame that is meant to support on the ground from the said position of use;

The self-support chassis of the movable part includes running gear, such as rollers or even omnidirectional wheels on its lower part, preferably lockable ones, making it possible to take out the removable part of the machine by having it roll on the ground.

The invention again involves a set including a treatment machine according to the invention and a wall separating a first enclosure with a controlled/non-controlled atmosphere from a second enclosure with a non-controlled/controlled atmosphere presenting a through-opening, and in which the said partitioning interfaced is fixed onto the wall set up in a way that locks the wall opening, and to allow, during the maintenance of the treatment system, the movable part of the treatment machine to be removed while the said partitioning interface of the treatment machine still locks the wall opening while the partitioning interface opening is locked by the second door system.

The invention again regards a maintenance procedure of a treatment machine for a set according to the invention in which a treatment system undergoes maintenance by taking the following steps:

Remove the movable part of the treatment machine while the said partitioning interface of the treatment machine still locks the wall opening, the said partitioning interface opening thus being locked by the door system, Transport the movable part to a remote maintenance workshop and review/repair the said treatment system, Return the reviewed/repaired movable part and set it up in its operating position immediately next to the partitioning interface.

According to a second general principle, the invention again regards a set including a machine for treating a medical apparatus, such as an endoscope washer-disinfectant and a separation wall, the said machine being integrated on the separation wall at a through-opening from the separation wall by locking it. The wall separates a first enclosure with controlled/non-controlled atmosphere from a second enclosure with non-controlled/controlled atmosphere.

On a single self-supporting chassis, the machine includes:
A treatment tank with a first opening configured to allow the loading/unloading of a medical device from the first enclosure and a second opening configured to allow the loading/unloading of a medical apparatus from the second enclosure, A first door system sealingly closing the first opening, A second door system sealingly closing the second opening, A treatment system of a medical apparatus with one or more treatment circuits, including one or more pumps, one or more solenoid valves, allowing the treatment of interior and exterior surfaces of the medical apparatus contained in the treatment tank by immersion and/or spraying, from a disinfectant solution sampled in a reservoir outside of the treatment tank.

A programmable controller system controlling the treatment system, particularly the motor and solenoid valves of the system, configured to implement a disinfection cycle of a medical device.

According to the invention, the set includes a door system hinged onto the wall which is configured to move from a first opening position for which the said door frees the opening of the wall in a position for using the machine for which the self-supporting chassis of the machine is positioned against the opening of the wall, thereby locking it in a second closing position authorizing the locking of the wall opening by locking it in a second closing position allowing the wall opening to be locked by the wall system after the treatment machine is removed.

The invention will be better understood after reading the description and looking at the designs attached, amongst which.

According to a first general principle, illustrated non-exhaustively in FIGS. 1 to 8, the invention also regards a treatment machine 1 of a medical apparatus such as an endoscope washer-disinfector intended to be integrated onto a wall M, the said separation wall at a through-opening $O_M$ of the separation wall.

This wall being intended to separate a first enclosure Sg with a controlled/non-controlled atmosphere, like a non-clean room of a second enclosure Sb with a non-controlled/controlled atmosphere, such as a clean room.

This treatment machine includes:
  A treatment tank 2 presenting a first opening 20 configured to allow the loading/unloading of a medical apparatus from the first enclosure Sg and the second opening 21 configured to allow the loading/unloading of a medical apparatus from the second enclosure Sb,
  A first door system 30 sealingly closing the first opening 20,
  A second door system 31 sealingly closing the second opening 21,
  The treatment system of a medical apparatus with one or more treatment circuits, including one or more pumps, one or more solenoid valves, making it possible to treat surfaces interior and exterior to the medical apparatus contained in the treatment tank 2 by immersion and/or by spray from a disinfectant solution taken from a reservoir such as a canister placed outside of the treatment tank,
  A programmable controller system controlling the treatment system, particularly the motor and the system solenoid valves, configured to implement the disinfection cycle of a medical device.

When the machine is in operating position, it is thus possible to load the treatment tank from a second enclosure such as a clean room of an operating room with a medical apparatus through the second opening, then to close the second door system. The apparatus contained in the tank is then disinfected, the first door system 30 and the second door system 31 then in closing position. The disinfected apparatus is then removed after opening the first door system from the first enclosure such as a non-clean room. It is also possible to do it the other way around, by loading the contaminated endoscope from the non-controlled atmosphere enclosure (the non-clean room) and unloading it into the controlled atmosphere room (the clean room).

According to an embodiment of the invention, the said machine 1 particularly includes an interface 4 of the enclosure intended to be fixed to the wall and a movable part 5, favorably removable from the partitioning interface during maintenance.

Here, by "fixed" we mean the fact that the partitioning interface is not removed during maintenance. This partitioning interface 4 is indeed meant to be fixed to the wall M and configured in a way that always blocks the $O_M$ configuration of the wall.

The said partitioning interface 4 includes at least one through-opening 40 intended to face the second opening 21 of the tank 2, at least in operating position P1 of the treatment machine.

Most notably the second door system 31 is secured to the said partitioning interface 4 (and not the movable part defined below), locking in its closing position the said opening 40 of the partitioning interface.

The movable part 5 is preferably removable from the partitioning interface 4 and contains a self-supporting, onboarding at least a part of the pump(s) and solenoid valves of the said medical apparatus treatment system as well as the said programmable controller system. In other words, this movable part 5 onboards the electrical and hydraulic systems of the machine that typically requires maintenance.

Figure 1:
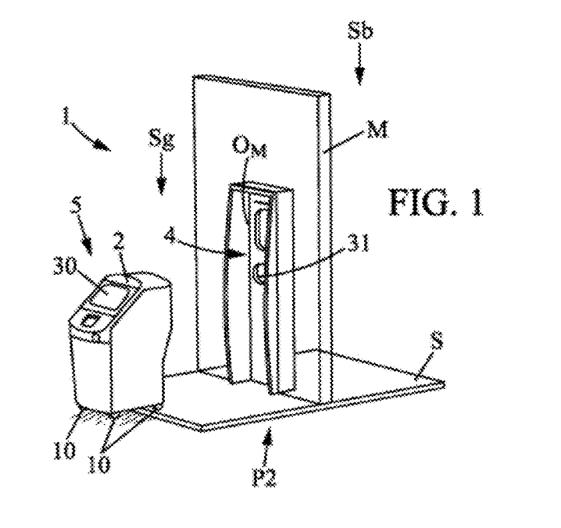
FIG. 1 is an overview according to a first embodiment including a treatment machine according to the invention, more particularly illustrating the movable part of the machine that supports the treatment tank, in a position removed and isolated from the enclosure, which is fixed to the separating partition.
Figure 2:
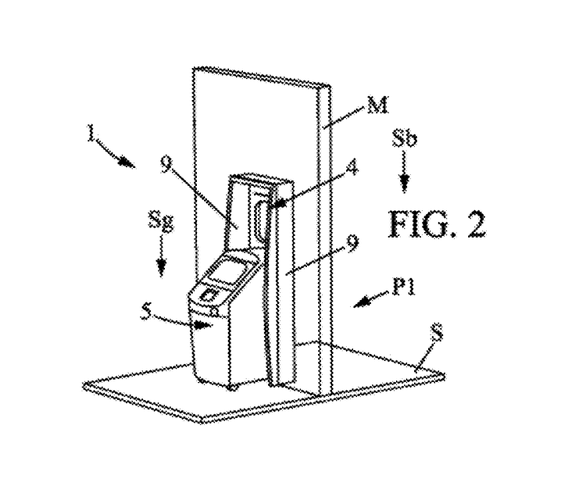
FIG. 2 is an overview according to FIG. 1 in the operating position of the machine for which the movable part is placed against the partitioning interface.

This movable part 5 is configured to position itself within immediate proximity to the partitioning interface 4 in operating position P1 of the treatment machine (visible in FIG. 2), and can be removed in a position P2 (visible in FIG. 1).

Favorably it is thus possible during maintenance on the treatment system to remove the movable part 5 of the treatment machine while the said partitioning interface 4 of the treatment machine still locks the wall opening, opening 40 of the partitioning interface 4 thus locked by the second door system 31.

It is therefore still possible to maintain a sealed separation between the first enclosure Sg, like the non-clean room, and the second enclosure, such as the clean room, compatible with the implementation of a control of the air quality in one of the enclosures, namely the controlled atmosphere one.

The clean room Sb usually has a controlled atmosphere by air purification (for example by HEPA filtration) and is removed from the enclosure: keeping a proper seal from the separation wall (even after removing the movable part 5) makes it possible to guarantee the quality of the atmosphere, even during heavy maintenance.

The invention also regards a set containing a treatment machine 1 according to the invention and a wall M separating a first enclosure Sg with a controlled/non-controlled atmosphere from a second enclosure Sb with a non-controlled/controlled atmosphere, presenting a through-opening $O_M$. In such an ensemble, the said partitioning interface 4 is fixed to the wall and configured so to lock the wall opening and make it possible to remove the movable part 5 of the treatment machine 1 during maintenance while the said partitioning interface 4 of the treatment machine still locks the opening $O_M$ of the wall, opening 40 of the partitioning interface thus blocked by the second door system 31.

The invention again regards a maintenance procedure of a treatment machine 1 for a set according to the invention, in which we perform maintenance on the treatment system by implementing the following steps:
  Removal of the movable part 5 of the treatment machine while the said partitioning interface 4 of the treatment machine still locks the opening Om of the wall, while the said opening 40 of the partitioning interface is locked by the second door system 30,
  Transport of the movable part to a remote maintenance workshop and review/repair of the treatment system, Return of the reviewed/repaired movable part 5 and implementation in its operating position P1 within the immediate proximity of the partitioning interface 4.

Eventually, and while the removed movable part 5 is being reviewed in the workshop, it is possible to place another movable part 5 (identical and of the same nature) in the operating position. This other movable part could, for example, be loaned by the review/repair provider in order to continue with the disinfection capacities during maintenance time. According to an embodiment, the movable part 5 onboards the treatment tank 2, a joint system 7 secured to the movable part 5, and/or secured to the interface of an enclosure 4 creating a seal between the second opening 21 of the tank 2 and the opening 40 corresponding to the partitioning interface 4 in the operating position P1 of the treatment machine. In this position P1 the second opening 21 of the tank 2 is placed to the partitioning interface 4 through the said joint system 7. This joint system 7 again makes it possible to remove the movable part 5 when extracted.

Figure 3:
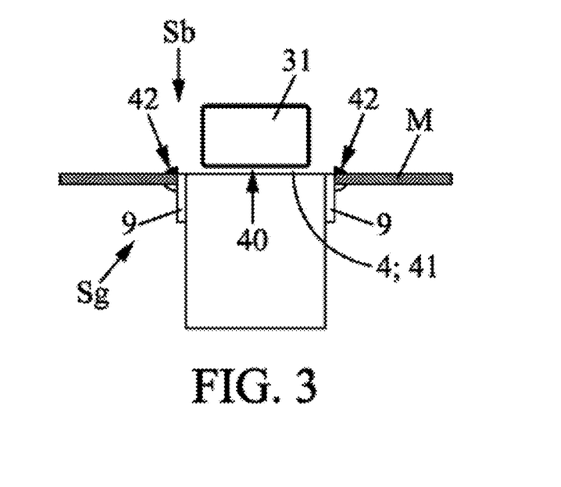
FIG. 3 is a schematic cut-away view according to a horizontal plane of the machine in an operating position of the first embodiment of the set.
Figure 4:
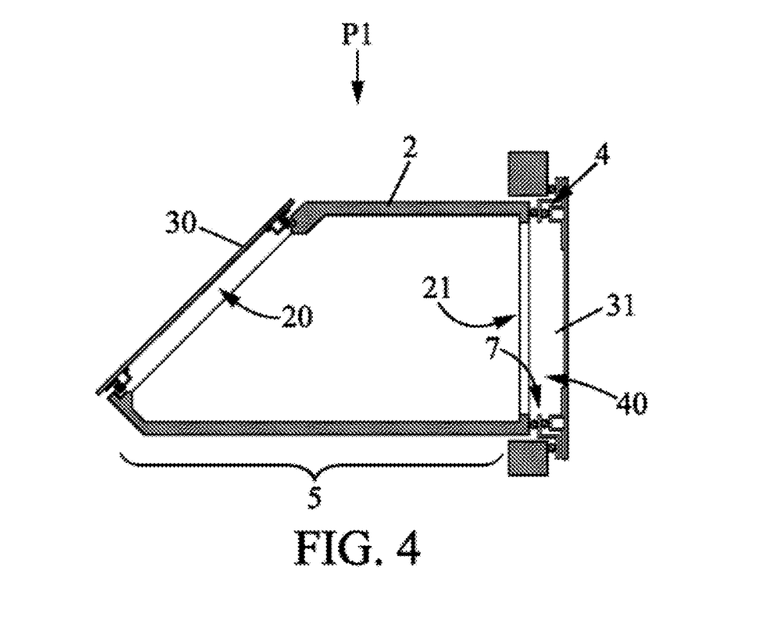
FIG. 4 is a schematic cut-away view according to a vertical plane of the machine in operating position, more particularly illustrating the joint system creating a seal between the second opening of the tank and the partitioning interface in the machine's said operating position, the joint system allowing the separation of these two parts when removing the movable part.
Figure 5:
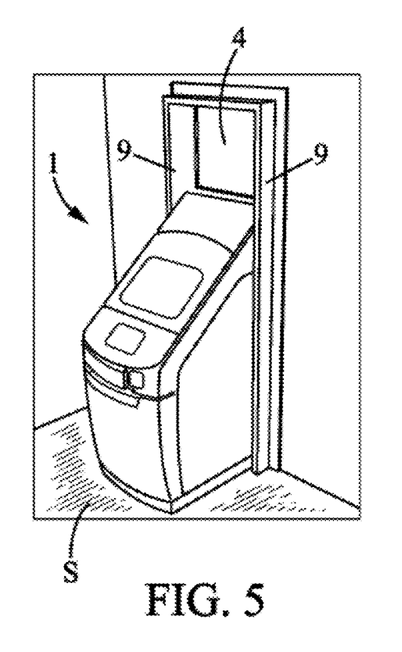
FIG. 5 and FIG. 6 are two views of both sides of the separation wall, of a machine in operating position, the said movable part placed against the partitioning interface in a position where the airtightness system creates a seal between the tank and the partitioning interface.
Figure 6:
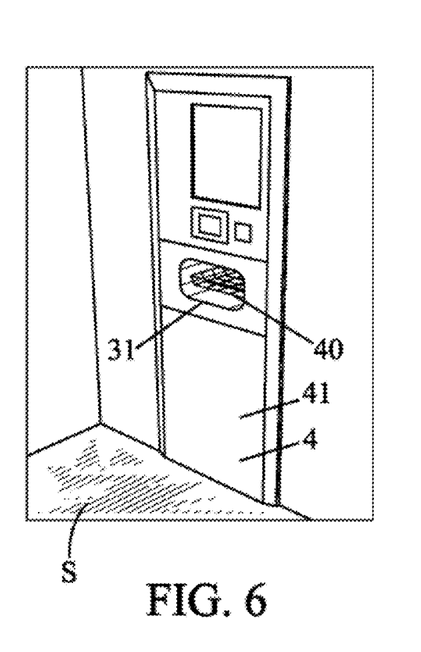

Such an embodiment is illustrated as an example in FIGS. 1 to 7, and more particularly in the FIG. 4 view. As schematically illustrated in FIG. 4, in the operating position P1, the second opening of the tank is plated against the opening 40 of the partitioning interface 4, via the joint system 7. In this position P1, the then-compressed joint system creates a seal between the partitioning interface and the second opening of partition, allowing the second door system 31 to lock the second opening 21. When the movable part 5 is removed, the joint system 7 is no longer compressed, at least partially.

Figure 8:
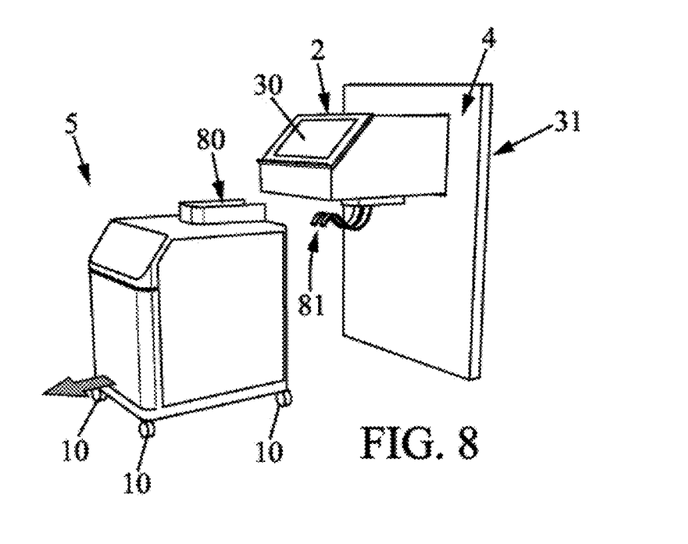
FIG. 8 is a view of the machine according to a second embodiment for which the treatment tank is secured to the partitioning interface, itself fixed to the wall.

According to another embodiment (alternative), illustrated as an example in FIG. 8, the treatment tank 2 is secured to the partitioning interface 4, a hydraulic connection system 80, 81 making it possible to connect the tubes or the circuits of the treatment system boarded onto the movable part 5, with the tubes of the circuit(s) of the treatment tank 2, in the said operating position P1 of the treatment machine, and to disconnect them while removing the movable part 5. This embodiment is different from the prior ones in that the treatment tank (as well as the first and second door system) is secured to the partitioning interface 4 and not the movable part.

The connection system 80, 81 is thus necessary to connect the conduits of the circuit(s) boarded onto the movable part 5 with the corresponding conduits of the treatment tank 2, and disconnecting them to allow the removal of the movable part 5.

Figure 7:
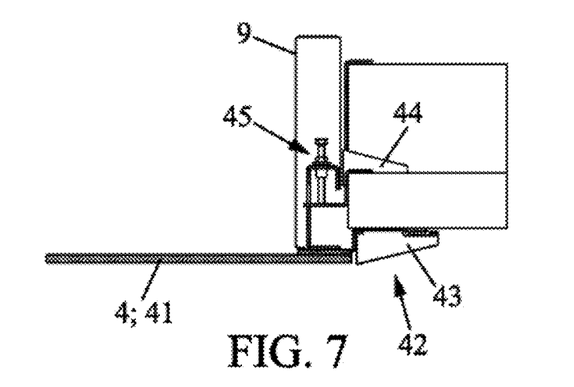
FIG. 7 is a view, according to a horizontal cut, of an embodiment of the peripheral fixation system of the partitioning interface, with a control system that makes it possible to adjust the mount to the wall's thickness.

According to a embodiment illustrated in FIG. 3 or FIG. 7, the partitioning interface 4 includes a partition 41 meant to run along the opening of the wall by blocking it reasonably parallel to the wall, as well as a system 42 for peripheral fixation secured to the partition, running along the strip of the wall opening, its mounts, and even its upper edge. This peripheral fixation system 42 can include, for each mount of the wall $O_M$:

- A first element 43 of the said support, such as an outline meant to push a side of the wall,
- A second element 44, a counter-support, intended to push the other side of the wall,
- A system 45 for adjustment and/or tightening (e.g. via screw), configured to adjust the gap between the first support element 43 and the second element 44 of counter-support for the thickness of the wall M, even to allow to press the wall between the first support element and the second counter-support element.

FIG. 7 illustrates as an example a system 45 of adjusting and tightening by screw which makes it possible to bring closer the first support element 43 to the second counter-support element 44 as well as to squeeze the wall.

According to an embodiment, the partitioning interface 4 can include a peripheral frame 9, serving as a cache, intended to stretch from the side of the partitioning interface 4 against that which is meant to position the chassis of the movable part 5 in operating position P1, along the length of the opening strips of the wall M and covering them, even protruding past the side of the wall on the side of the movable part 5.

The function of this frame is aesthetic, namely, to hide the days on both sides of the movable part, between each lateral wall of the frame and the strip of the corresponding opening. The interior walls of the frame 9 form a casing for the movable part 5, with a width adjusted to the size of the movable part 5 while the exterior walls of the frame 9 flush the strips of the wall opening.

According to a embodiment, the self-supporting chassis of the movable part 5 is a frame meant to support on the ground S in the said operating position P1. The self-supporting chassis of the movable part 5 can include running gear 10, such as rollers or even omnidirectional wheels on its lower part, preferable lockable, making it possible to remove the movable part 5 of the machine by making it roll on the ground S or the other way around by placing it against the partitioning interface.

Figure 9:
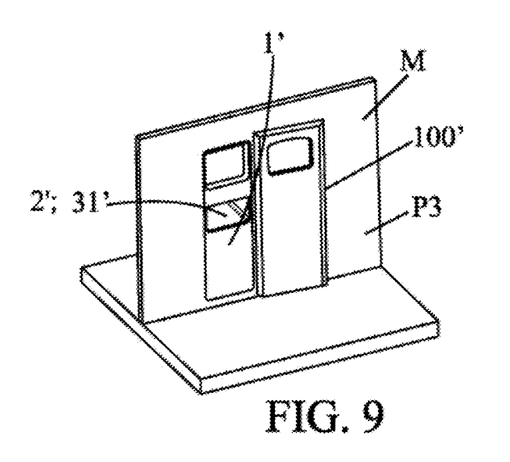
FIGS. 9 and 10 are two schematic views of a third embodiment for which a door system opens a wall opening when the treatment machine is in operating position in this wall opening and makes it possible to close this opening when the treatment machine is removed for maintenance.
Figure 10:
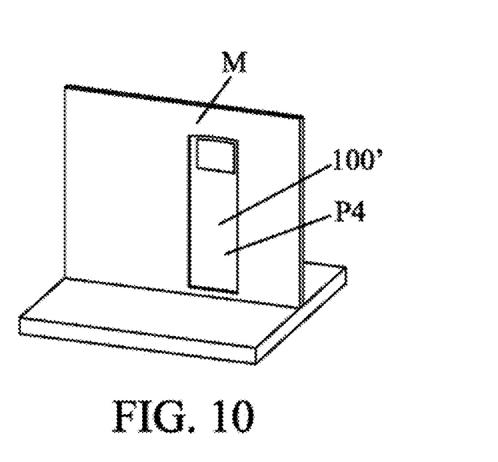

FIGS. 9 and 10 disclose a second general principle that makes it possible to respond to the problem posed by the invention.

The set illustrated in FIGS. 9 and 10 includes a treatment machine of a medical apparatus, such as an endoscope washer-disinfector, and a separation wall M, the said machine being integrated onto a wall, the said separation wall at the level of a through-opening of the separation wall by locking it, the wall separating a first enclosure Sg with controlled/non-controlled atmosphere from a second enclosure Sb with non-controlled/controlled atmosphere, The machine is contiguous and contains, on the same self-supporting chassis:
- A treatment tank with a first opening configured to make it possible to load/unload a medical device from the first enclosure and a second opening configured to allow the loading/unloading of a medical device from the second enclosure,
- A first door system making it possible to sealingly close the first opening,
- A second door system making it possible to sealingly close the second opening,
- A treatment system for a medical apparatus presenting one of several treatment circuits, including one or several pumps, one or several solenoid valves, making it possible to treat the interior and exterior surfaces of the medical apparatus contained in the treatment tank by immersion and/or by spraying, from a disinfectant solution taken from a reservoir outside of the treatment tank,
- A programmable controller system controlling the treatment system, particularly the motor and solenoid valves of the system, configured to implement a disinfection cycle of a medical apparatus.

According to this second principle, the said set includes a door system 100 hinged (for example by hinges or sliders) to the wall which is configured to move from a first opening position P3 for which the said door releases the opening of the wall M in the operating position of the machine 1' for which the self-supporting chassis of the machine is positioned against the wall opening by locking it to a second closing position P4, making it possible to lock the wall by the door system 100 after the treatment machine is removed.

The principle illustrated in FIGS. 9 and 10 requires, after removing the machine 1' for reasons of maintenance, closing the door system 100' for locking the opening of the wall left gaping open when the machine 1' was removed, which is less satisfying in terms of security than the first general principle of FIGS. 1 to 8, which is based on the use of a machine including a partitioning interface fixed to the wall and configured to always lock this opening $O_M$.

NOMENCLATURE

Principle of FIGS. 1 to 8:
1. Treatment machine,
2. Treatment tank,
20, 21. First and second opening of the tank,
30, 31. First door system and second door system,
4. Partitioning interface,
40. Opening of the partitioning interface intended to be positioned facing the second opening of the tank,
41. Partition,
42. Peripheral fixation system,
43. 44. First support element and second counter-support element,
45. Adjustment and tightening system,
5. Movable part, removable with regard to the partitioning interface,
7. Hinge system between the tank and the partitioning interface (embodiment of FIGS. 1 to 7),
9. Frame
10. Running gear
80, 81. Hydraulic connection system between the conduits of the treatment tank, secured to the partitioning interface and the tubes of the treatment system boarded onto the movable part (embodiment of FIG. 8)
M. Separation wall,
$O_M$. Through-opening (Wall)
Sg, Sb. First enclosure such as a non-clean room, and a second enclosure such as a clean room separated by the wall,
S. Ground.
P1. Operating position of the machine for which the movable part is immediately adjacent and is connected to the partitioning interface (physically or hydraulically),
P2. Maintenance position of the machine for which the movable part is removed.
Principle of FIGS. 9 and 10.
1'. Treatment machine,
M'. Separation wall,
Sg', Sb'. First enclosure such as the non-clean room, and second enclosure such as the clean room separated by the wall,
100'. Door system
P3. First opening position of the door system,
P4. Second closing position of the door system.

The invention claimed is:

1. A machine for treating a medical apparatus comprising:
a treatment tank having a first opening configured to allow a medical apparatus to be loaded into/unloaded from a first enclosure and a second opening configured to allow the medical apparatus to be loaded into/unloaded from a second enclosure,
a first door system sealingly closing the first opening,
a second door system sealingly closing the second opening,
a treatment system for treating the medical apparatus comprising one or more treatment circuits including one or more pumps and one or more solenoid valves, the treatment system being configured to treat the medical apparatus contained in the treatment tank with a disinfectant solution,
a partitioning interface configured to be attached to a wall having an opening, the partitioning interface being configured to close the opening of the wall, the partitioning interface comprising at least one through-opening, wherein, when the machine is in an operating position, the second door system is secured to the through-opening of the partitioning interface,
a movable part configured to be removed from the partitioning interface, the movable part comprising a self-supporting frame and at least partially carrying the one or more pumps and the one or more solenoid valves of said treatment system, the movable part being configured to assume a position immediately adjacent to the partitioning interface when the treatment machine is in the operating position,
and, wherein, when the movable part of the treatment machine is removed from the partitioning interface, the partitioning interface locks the opening of the wall and the second door system locks the through-opening of the partitioning interface, thereby allowing the movable part of the treatment machine to be removed for maintenance.

2. The machine according to claim 1, wherein the movable part carries the treatment tank, and further comprising a joint system secured onto at least one of the movable part and the partitioning interface, the joint system creating a seal between the second opening of the treatment tank and the through-opening of the partitioning interface, and when the treatment machine is positioned in the operating position, the second opening of the treatment machine being engaged with the partitioning interface via the joint system.

3. The machine according to claim 1, wherein the treatment tank is secured to the partitioning interface, and further comprising a hydraulic connection system configured to connect one or more tubes of the one or more circuits of the treatment system carried by the movable part with one or more corresponding tubes of the treatment tank, thereby allowing the one or more tubes carried by the movable part to be disconnected from the one or more corresponding tubes of the treatment tank, when removing the movable part.

4. The machine according to claim 1, wherein the partitioning interface further comprises a partition and a peripheral fixation system, the partition being configured to run along the opening of the wall and block the opening, the peripheral fixation system being secured about a perimeter of the partition.

5. The machine according to claim 4, wherein the peripheral fixation system comprises:
a first support element configured to push on one side of the wall,
a second counter-support element configured to push against an other side of the wall, and
a tightening system configured to adjust a space between the first support element and the second counter-support element to a thickness of the wall.

6. The machine according to claim 4, wherein the partitioning interface includes a peripheral frame configured to stretch from a side of the partitioning interface against which a self-supporting chassis of the movable part is configured to be placed when in the operating position, wherein interior walls of the peripheral frame form a casing for the removable part, the width of which is adjustable to a size of the movable part.

7. The machine according to claim 1, wherein the self-supporting fame of the movable part is configured to be supported by the ground, when in the operating position.

8. The machine according to claim 7, wherein the self-supporting frame of the movable part comprises a running gear on its lower part, making it possible to remove the movable part of the machine by making it roll on the ground.

9. An installed treatment system comprising:
the treatment machine according to claim 1, and
the wall separating the first enclosure with a controlled/non-controlled atmosphere from the second enclosure with a non-controlled/controlled atmosphere,
wherein the wall contains the opening, and
the partitioning interface is fixed to the wall and configured to lock the opening of the wall, and to allow, during maintenance on the treatment system, the movable part to be removed from the treatment machine while the partitioning interface of the treatment machine still locks the opening of the wall and the through-opening of the partitioning interface is locked by the second door system.

10. A maintenance procedure for the installed system according to claim 9, wherein the treatment system is maintained by implementing at least the following steps:
removing the movable part of the treatment machine while the partitioning interface of the treatment machine still locks the opening of the wall and the opening of the partitioning interface is locked by the second door system,
transporting the movable part to a remote maintenance workshop for at least one of review and repair of the treatment system, and
reinstalling the movable part in its operating position immediately adjacent to the partitioning interface.

11. A system comprising:
a treatment machine of a medical apparatus,
a separation wall,
the treatment machine being integrated onto the separation wall and locked into a through-opening of the separation wall; the separation wall separating a first enclosure with a controlled/non-controlled atmosphere from a second enclosure with a non-controlled/controlled atmosphere,
the treatment machine comprising a self-supporting chassis carrying at least:
a treatment tank having a first opening configured to allow a medical apparatus to be loaded into/unloaded from the first enclosure and a second opening configured to allow the medical apparatus to be loaded into/unloaded from the second enclosure,
a first door system sealingly closing the first opening,
a second door system sealingly closing the second opening,
a treatment system for treating the medical apparatus comprising one or more treatment circuits, including one or more pumps and one or more solenoid valves, the treatment system being configured to treat the medical apparatus contained in the treatment tank with a disinfectant solution,
a door system hinged to the wall, the door system being configured to move from a first opening position in which the door releases the opening in the wall and the self-supporting chassis of the treatment machine is locked into the opening to a second closing position in which the door is locked to the opening in the wall after the removal of the treatment machine.

12. The system according to claim 11, wherein the medical apparatus is an endoscope.

13. The machine according to claim 1, wherein the medical apparatus is an endoscope.

* * * * *

UNITED STATES PATENT AND TRADEMARK OFFICE
CERTIFICATE OF CORRECTION

PATENT NO. : 11,051,687 B2  
APPLICATION NO. : 16/465945  
DATED : July 6, 2021  
INVENTOR(S) : Christian Affre, Jean-François Biry and Sébastien Ruiz Page 1 of 1

It is certified that error appears in the above-identified patent and that said Letters Patent is hereby corrected as shown below:

In the Claims

In Column 11, Claim 6, Lines 1-2, delete "removable" and insert -- movable --

In Column 11, Claim 7, Line 5, delete "fame" and insert -- frame --

In Column 12, Claim 11, Line 6, delete "wall;" and insert -- wall, --

Signed and Sealed this  
Twenty-eighth Day of December, 2021

Drew Hirshfeld  
*Performing the Functions and Duties of the*  
*Under Secretary of Commerce for Intellectual Property and*  
*Director of the United States Patent and Trademark Office*